(12) United States Patent
Stephan et al.

(10) Patent No.: US 6,699,954 B2
(45) Date of Patent: Mar. 2, 2004

(54) MONOMERS, POLYMERS INCORPORATING SAID MONOMERS AND THEIR USE IN ORGANIC ELECTROLUMINESCENT DEVICES

(75) Inventors: Olivier Stephan, Le Touvet (FR); Michel Armand, Montreal (CA); Jean-Claude Vial, Grenoble (FR)

(73) Assignee: Universite Joseph Fourier, Grenoble (FR)

( * ) Notice: Subject to any disclaimer, the term of this patent is extended or adjusted under 35 U.S.C. 154(b) by 0 days.

(21) Appl. No.: 10/098,060

(22) Filed: Mar. 14, 2002

(65) Prior Publication Data

US 2002/0099157 A1 Jul. 25, 2002

Related U.S. Application Data

(63) Continuation of application No. PCT/FR00/02538, filed on Sep. 14, 2000.

(30) Foreign Application Priority Data

Sep. 15, 1999 (FR) .............................................. 99 11702

(51) Int. Cl.⁷ .............................................. C08F 116/12
(52) U.S. Cl. ........................ 526/333; 526/256; 526/260; 526/265; 526/279; 526/280; 526/284; 526/310; 526/312; 568/38
(58) Field of Search .............................. 568/38; 526/256, 526/260, 265, 279, 280, 284, 310, 312, 333

(56) References Cited

U.S. PATENT DOCUMENTS 4,226,967 A 10/1980 Tazuke et al. ................. 528/74
5,708,130 A 1/1998 Woo et al. ................... 528/397

FOREIGN PATENT DOCUMENTS

WO  WO 97/33323  9/1997

OTHER PUBLICATIONS

Klavetter et al. Polymeric Materials Science and Engineering (1993), 69, 153–4.*
Winkler et al. Chemistry of Materials (1999), 11(3), 704–711.*
D. Hwang et al, "New Luminescent Polymers for LEDs and LECs," *Macromol. Symp. 125, 111–20* (1997).
B. S. Chuah et al, "New Luminescent Polymers for LEDs," *Synthetic Metals, 91, 279–82* (1997).
R. O. Garay et al, "Synthesis and Characterization of Poly [2,5–bis(triethoxy)–1,4–phenylene vinylene],"*J. Polymer Science, Part A: Polymer Chemistry, 33, 525–31*(1995).

* cited by examiner

*Primary Examiner*—Helen L. Pezzuto
(74) *Attorney, Agent, or Firm*—Heslin Rothenberg Farley & Mesiti P.C.

(57) ABSTRACT

The invention concerns a monomer of general formula A—(Q—S)$_p$ wherein: A=an aromatic or heteroaromatic ring; Q=a carbonaceous or siliceous divalent radical, respectively corresponding to general formulae: $(CR^1R^2)_n$ wherein: $R^1$, $R^2$=H, alkyl, alkenyl comprising between 1 to 4 carbon atoms and n ranges between 4 and 24; and $[O—Si(R^1R^2)]_n$ wherein $R^1$, $R^2$=H, alkyl, alkenyl comprising between 1 and 4 carbon atoms and n ranges between 3 and 24; S=a solvating segment consisting of at least an aliphatic chain comprising at least a polar heteroatom. $1 \leq p \leq 6$. The invention also concerns the polymer (homopolymer or copolymer) incorporating said monomer, and their use in organic electroluminescent devices.

7 Claims, No Drawings

MONOMERS, POLYMERS INCORPORATING SAID MONOMERS AND THEIR USE IN ORGANIC ELECTROLUMINESCENT DEVICES

CROSS REFERENCE TO RELATED APPLICATIONS

This application is a continuation of PCT application PCT/FR00/02538 filed Sep. 14, 2000 designating the United States, and published in French as WO 01/19765 on Mar. 21, 2001. PCT/FR00/02538 claimed the priority of French application FR 99/11702 filed Sep. 15, 1999. The entire disclosures of both are incorporated herein by reference.

The invention relates to a novel monomer and to the polymer (homopolymer or copolymer) incorporating said monomer, and to their use in organic electroluminescent devices.

Among organic electroluminescent devices, a distinction is made between electroluminescent diodes, also known by the term LED, signifying light emitting diode, and electroluminescent electrochemical cells, also denoted LEC, signifying light emitting electrochemical cell.

LEDs and LECs are well known and correspond to emitters consisting of a thin polymer layer defining a so-called active zone, which is sandwiched between two electrodes, a cathode and an anode respectively, of which at least one is transparent or semitransparent so as to facilitate observation of the luminous emission. The thin film structure of these emitters is particularly advantageous for diffuse lighting and flat screens.

In practice, the semitransparent anode is made of ITO, signifying indium tin oxide, resulting from the doping of $In_2O_3$ with $SnO_2$, or of tin oxide doped with antimony or fluorine ($SnO_2$:Sb or $SnO_2$:F), while the cathode is made of aluminum.

The polymers employed within the active zone are so-called conjugated polymers, i.e., polymers whose constituent monomers exhibit an alternation of single bonds, called σ bonds, and double bonds, called π bonds, leading to a system of π electrons which is highly delocalized along the carbon chain.

Compounds of this kind are derived principally from polyacetylene or else obtained by catenating aromatic nuclei such as benzene, naphthalene, pyrrole, thiophene, pyridine, quinoline, anthracene, carbazole, and fluorene.

In some cases, to allow the steric stresses to be reduced and so to maintain the aromatic entities within the same plane, the abovementioned nuclei are coupled by way of a —(CH=CH)—vinylene bond.

From an electrochemical standpoint, the conjugated polymers can be oxidized or reduced for a structural rearrangement of the alternation of their bonds. More specifically, oxidation, i.e., the loss of an electron, can be interpreted as the making of a hole in the valence band (HOMO), or "p" doping of the material. Similarly, reduction, which consists in adding an electron, can be interpreted as being the provision of an electron in the conduction band (LUMO), or "n" doping. Consequently, the difference between the oxidation potential and reduction potential of the conjugated polymer can be analyzed as corresponding to the gap of the polymer as a semiconductor material.

Owing to its semiconducting properties, this type of polymer can be employed in the abovementioned organic electroluminescent devices, the phenomenon of electroluminescence resulting from the radiative recombination of an electron from the conduction band and a hole from the valence band, with the carriers (holes and electrons) being injected into the active layer when a potential is applied between the two electrodes.

LEDs and LECs differ in the composition of their active zone.

Accordingly, while the active zone of LEDs consists exclusively of a polymer containing no conductivity additive, which is obtained in film form from a solution in a solvent or by evaporation under vacuum, the layer of the LECs also comprises a salt and a solvent for this salt which is mixed with the conjugated polymer or grafted onto it.

The effect of this difference in composition is to impart different operating voltages to these two devices. Thus with regard to LEDs it is necessary to apply a high operating voltage of more than 10 volts, whereas an operating voltage of between 3 and 4 volts is sufficient for LECs.

The high voltage required for operating LEDs is due, to the very low conductivity of the polymers, which are used in the undoped state, and to the nonohmic nature of the contacts between polymer and electrodes, this nonohmic nature resulting from the existence of potential barriers.

The addition of a salt to the thin layer of the LECs allows the height of this potential barrier to be reduced in accordance with the following phenomenon.

When a low potential is applied between the anode and the cathode, the ions from the dissociated salt migrate toward the electrodes in question to form two fine, charged layers at the interface of the active medium and the electrodes, and these layers will promote the injection of electrons and holes, making the polymer conductive at the polymer/electrode interfaces. When the applied potential exceeds the threshold voltage, the electrons and the holes are injected respectively into the anode/active layer and cathode/active layer interfaces, thereby initiating the formation of a p-n junction. When the voltage is increased again, the additional electrons and holes injected migrate under the effect of this potential excess toward the cathode and the anode. The radiative recombination of these carriers within the space charge zone constitutes the origin of the phenomenon of electroluminescence.

When doping is sufficient, contact between the electrodes and the polymer is ohmic in character, such that the operating voltages are reduced considerably and are close to the theoretical value, viz. the energy difference between the valence band (HOMO) and the conduction band (LUMO) of the polymer.

However, producing the thin layer or active zone of LECs is not simple, on account of the fact that said layer is likely to contain a hydrophobic polymeric material, which is virtually nonpolar, and an ionic species, which undergoes appreciable dissociation only in the presence of a polar solvent.

In order to allow the mixing of the hydrophobic polymer with the hydrophilic salt, it has been proposed that cations and anions resulting from the dissolution of the salt be solvated.

To do this, one first solution consists in solvating the salt, such as the lithium salt, for example, of trifluoromethanesulfonic acid ($LiCF_3SO_3$) by means of a solvating polymer of the poly(ethylene oxide) type. However, the two polymers are immiscible, and even less compatible in the presence of salt, so that the mixture obtained is in heterogeneous form.

Another method, which is described in the document WO 97/33326, consists in grafting solvating segments of oligo (ethylene oxide) type onto the frame of a conjugated polymer of the fluorene type. Although this type of compound does make it possible to solve the problem of inhomogeneity of the polymer mixture (phase microseparation), the conjugation which exists between the various monomer units is liable, however, to be modified.

In effect, the solvating segments of oligo(ethylene oxide) type induce a local disorder which—necessary for ionic conduction—is manifested in a loss of coplanarity of the units which allow the π conjugation. In addition, the local disorder is further accentuated by the addition of an ionic compound, the lateral chains being arranged in priority in order to ensure the salvation of the Li⁺ cations. Moreover, the energy employed by this process (greater than 60 KJ) is markedly greater than the energy gain obtained by virtue of the extension of the π conjugation (greater than 10 KJ).

Thus, for example, polythiophenes substituted in position 3 by oligo(ethylene oxide) groups with a mass close to 200 change their optical absorption spectrum by passing from the violet to the yellow in the presence of alkali metal cations, thereby demonstrating the loss of the π conjugation.

In parallel, the reduction in conjugation is detrimental to the electronic conductivity, which requires a local order, and to the fluorescence and luminescence.

Furthermore, the reduction in conjugation makes things more difficult for "n" and "p" doping, which takes place at potentials which are more cathodic and more anodic than the polymers which are not substituted by oligo(ethylene oxide) segments. Consequently, the doped materials are less stable, especially toward agents such as water or atmospheric oxygen.

Finally, the $OCH_2CH_2$ groups, corresponding to the direct fixation of the oligo(ethylene oxide) segments on the polymer, have an attractive power which is due to the electronegativity of the oxygen, and which therefore contributes to making "p" doping more difficult.

The problem which the invention aims to solve is to provide a monomer having an aromatic nucleus which is equipped with solvating segments, which can be polymerized, and which does not have the disadvantages described above.

The invention accordingly provides a monomer of general formula $$A—(Q—S)_p,$$

where:
- A=aromatic or heteroaromatic nucleus,
- Q=carbon-based or silicon-based divalent radical,
- S=aliphatic chain containing at least one polar heteroatom, and

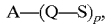

In other words, the invention consists in having separated the aromatic nucleus A from the monomer of the solvating segment S by the intermediacy of a flexible chemical link Q, thereby allowing spatial separation of the solvating functions from the functions linked to the conjugation. This solution enables the problems set out above to be solved. In effect, the conjugated system is able to adopt a planar conformation which is therefore optimal for its properties of conjugation, doping, conductivity, and luminescence. Independently of any strain on the conjugated system, the solvating segments are able to undergo conformation to provide optimum salvation of the cations and hence better ionic conduction. Since the spacer arm Q is not an electron attracter, it has very little influence on the doping potential, which also makes it possible here to retain stability in the doped polymer.

According to a first feature of the invention, A is selected from the group consisting of the nuclei phenyl, naphthalene, pyrrole, thiophene, benzo-thiophene, pyridine, quinoline, carbazole, anthracene, and fluorene.

In order to improve the conjugation of the system of delocalized π electrons, the aromatic or heteroaromatic nucleus A may be engaged in different types of bonds.

This bond may, for example, be in the form of a chain containing 2n atoms, such as C or N, and "n" double bonds conjugated with S.

Among these bonds, it is advantageous to employ bonds of the vinylene type $(CR=CH)_n$, where n is between 1 and 5 and R=H, alkyl or aryl containing 1 to 12 carbon atoms. In this case, A is selected from the group consisting of vinylene-phenyl, vinylene-naphthalene, vinylene-pyrrole, vinylene-thiophene, vinylene-benzo-thiophene, vinylene-pyridine, vinylene-quinoline, vinylene-carbazole, vinylene-fluorene, and vinylene-anthracene.

The bond may also be an azomethine bond $(CR=N)_n$ or else an azo bond $(N=N)_n$.

According to another feature of the invention, the monomer, as already stated, has solvating segments S in the form of an aliphatic chain containing at least one polar heteroatom such as O, N, S or P which possesses free electronic doublets capable of interacting with the cations resulting from the dissociation of the salt.

According to a first embodiment, the aliphatic chain S is a polyether of general formula:

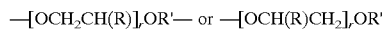

where
- r is between 1 and 50
- R=H or alkyl containing from 1 to 6 carbon atoms
- R'=alkyl, alkenyl, aryl, arylalkyl or alkenylaryl containing from 1 to 30 carbon atoms.

In a second embodiment, S is a polyamine corresponding to the general formula:

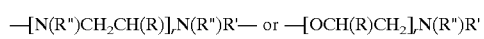

in which:
- r is between 1 and 50
- R and R"=H or alkyl containing 1 to 6 carbon atoms
- R'=alkyl, alkenyl, aryl, arylalkyl or alkenylaryl containing from 1 to 30 carbon atoms.

In one advantageous embodiment, S is a polyether corresponding to the general formulae above and for which R=R"=H or $CH_3$ and R'=methyl, ethyl, butyl, hexyl, octyl, dodecyl, tetradecyl, hexadecyl benzyl.

As already stated, in order to obtain better conductivity of the monomer, the solvating segments are separated from the aromatic nucleus by the intermediacy of flexible bonds.

In a first embodiment, the divalent radical Q constituting the flexible chemical bond corresponds to the general formula $(CR^1R^2)_n$, in which $R^1$ and $R^2$=H, alkyl or alkenyl containing between 1 and 4 carbon atoms and n is between 4 and 24.

The flexible bond Q advantageously has the general formula $(CH_2)_n$ in which n is between 4 and 24 carbon atoms.

In another embodiment, the divalent radical Q constituting the flexible chemical bond corresponds to the general formula $[(O—Si(R_1R_2)]_n$ in which $R_1$ and $R_2$=H, alkyl or alkenyl containing between 1 and 4 carbon atoms and n is between 3 and 24.

Furthermore, and according to another characteristic, the monomer of the invention has functions allowing its subsequent polymerization, such as, for example, halogen, amine or aldehyde functions which allow a polycondensation.

In advantageous embodiments, the monomer of the invention is 2,7-dibromo-9,9-bis(7,10,13,16-tetraoxa-heptadecyl) fluorene or 2,7-dibromo-9,9-bis(5,8,11-tri-oxadodecyl) fluorene.

Accordingly, the invention further provides a polymer of homopolymer or copolymer type incorporating the monomer of the invention. This polymer may be random, of random nature, alternating or of alternating nature, block or of block nature.

The methods which allow the coupling and hence the polymerization of the monomers of the invention, either directly or by the intermediacy of the bonds set out above (in particular of the vinyl type), are perfectly well known to the skilled worker.

Mention may be made, for example, of the coupling of monomers bearing two halogen or pseudohalogen groups in the presence of a reducing agent and a catalyst, examples being derivatives of 2,2'-bipyridine or else derivatives of nickel or of palladium complexed with tertiary phosphines.

The monomers having vinylene bonds are obtained by eliminating a sulfonium group obtained from the derivative halogenated in a basic medium in accordance with the following reaction:

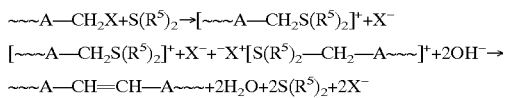

in which:

X represents a halogen or a pseudohalogen, Cl, Br, I, SCN, $NO_2$, $CF_3SO_2$, or $CF_3SO_3$.

$R^5$ represents an alkyl group of 1 to 4 carbon atoms, or else two groups $R^5$ are combined with the sulfur to form a ring, especially when $S(R^5)_2$ is tetrahydrothiophene.

~~~ represents the growing macromolecular chain.

It is also possible to bring about polymerization by duplicative elimination:

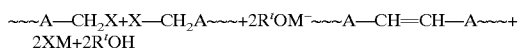

in which:

X has the above meanings $R^t$ is a tertiary organic carbon radical

M is an alkali or alkaline earth metal $R^t$ is preferably the tert-butyl or tert-amyl group.

The invention likewise provides an organic electroluminescent device consisting of a thin layer comprising the polymer of the invention, said layer being sandwiched between two electrodes.

The electroluminescent polymer may of course be integrated into the active zone of both LEDs and LECS.

In the remainder of the description, however, the polymer of the invention is more particularly used in LECS. In this type of device, the thin layer comprises not only the polymer but also a salt.

Accordingly, and as already stated, the creation of an ohmic junction at the interfaces with the electrodes, and the absence of space charges, result from the formation of doped layers n and p respectively at the negative electrode and the positive electrode.

The polymer of the invention, by virtue of the separation of the solvating segments and the aromatic nuclei, makes it possible to obtain optimum conjugation of the π system while respecting the salvation characteristics provided by the groups S.

In practice, the cations resulting from the dissociation of the salt contained within the thin layer constituting the active zone of the LEC are selected from the group consisting of metal cations and omnium type cations. Among the metal cations, a selection is made of the cations derived from rare earths and from transition metals, advantageously the cations derived from alkali metals and from alkaline earth metals.

Moreover, the expression "cations of onium type" denotes the cations ammonium $(NRi_4)^+$, phosphonium $(PRi_4)^+$, amidinium $(RC(NRi_2)_2)^+$ or guanidinium $(C(NRi_2)_3)^+$ where R and Ri=H, alkyl or aryl containing 1 to 18 carbon atoms.

The solubility of the salts corresponding to the aforementioned cations, and also the dissociation and conductivity, of course depend heavily on the corresponding anion. Particular preference will be given to anions of low basicity which correspond to the strong acids. Among these, selection will be made in particular of $ClO_4^-$, $BF_4^-$, $PF_6^-$, $AsF_6^-$, $SbF_6^-$, $TeOF_5^-$, $RSO_{3-}$, $(RSO_2)_2N^-$ or $(RSO_2)_2CY^-$, in which R is a principally perfluorinated radical containing from 1 to 8 carbon atoms and Y=H, CN or $RSO_2$.

According to another feature, the material of the transparent electrode is selected from the group consisting of zinc oxide doped with metallic zinc, gallium, zirconium, tin oxide doped with fluorine or antimony, indium oxide doped with tin, antimony, and fluorine.

As is known, these oxides can be deposited either on layers of glass or a polymer or directly on the electroluminescent material, i.e., the polymer of the invention, via techniques such as cathodic sputtering.

Furthermore, it is also advantageous to select at least one electrode having a high reflective power, consisting preferably of a metal or alloy.

Use is made in particular of a metal selected from the group consisting of aluminum, gold, silver, tin, lead, beryllium, magnesium, calcium, barium, and their alloys.

In order to increase the adhesion or immobilize the active molecules electrochemically or optically, the electrodes may advantageously be surface treated by sizing processes, in particular with organosilanes.

Similarly, in order to modify the injection properties of the carriers (electrons and holes), the electrodes are covered with a layer of an organic or inorganic material.

In one advantageous embodiment, the compound constituting the layer facilitating the injection of carriers is selected from the group consisting of polyquinolines, polycarbazoles, polymers possessing aromatic nuclei linked by cyanovinylene groups C(CN)=CH—, polyanylines, polythiophenes, and especially those possessing phenyl ether substituent functions in position 3 and/or ether substituent functions in position 4, fluorides, such as LiF and $MgF_2$, oxides such as MnO, and nitrides such as AlN or $Si_3N_4$.

The derivatives of the monomers of the invention may have various adjuvants added to them. These can be solid particles such as ceramic nanoparticles, oxides such as silica, alumina $Al_2O_3$, $LiAlO_2$, ZnO, and $SnO_2$, or nitrides such as AlN. They can also be polymers in the form of latices or fibers, such as polystyrene, polyvinylpyrrolidinone, polyvinylpyridine, polypropylene, and polyethylene. It is also possible to envisage the addition of polyethylene oxides and copolymers thereof, in the presence where appropriate of dispersants, and the addition of plasticizers such as esters of organic polyacids, ethers, and esters of oligo(ethylene oxide).

The invention and the advantages which result from it will emerge more clearly from the following embodiment examples.

EXAMPLE 1

Synthesis of the copolymer poly[(9,9-bis(7,10,13,16-tetraoxaheptadecyl)fluorene-co-9,9-(dihexyl)fluorene)]

1/Synthesis of the functional group 1-bromo-7,10,13,16-tetraoxaheptadecyl

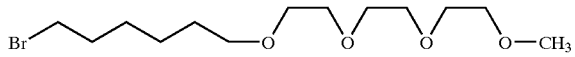

4.92 g (30 mmol) of triethylene glycol monomethyl ether are diluted in 80 ml of anhydrous tetrahydrofuran. Then 1 equivalent (0.72 g) of metallic sodium (Na) is added. The mixture is subsequently stirred at ambient temperature for 12 hours. The alkoxide thus formed is transferred to a dropping funnel and added dropwise at ambient temperature to a mixture of 50 ml of tetrahydrofuran and a large excess of dibromohexane (36.6 g or 5 equivalents). The reaction mixture is then left with stirring for 12 hours more. The organic solution thus obtained is neutralized with 10 ml of water. 1-Bromo-7,10,13,16-tetraoxaheptadecyl is then extracted with ether. This organic phase is then washed copiously with an aqueous solution. The organic phase is subsequently dried over $MgSO_4$ and then evaporated under reduced pressure. This gives a yellowish oil containing principally a mixture of 1-bromo-7,10,13,16-tetraoxaheptadecyl and dibromohexane in excess.

The mixture is purified by chromatography on a silica column in two steps: a first elution carried out with pentane removes the dibromohexane from the mixture. 1-Bromo-7,10,13,16-tetraoxaheptadecyl is subsequently liberated using a pentane/acetone mixture (50/50) as eluent. Evaporation gives a yellow-colored oil.

2/Synthesis of the monomer 2,7-dibromo-9,9-bis-(7,10,13,16-tetraoxaheptadecyl)fluorene

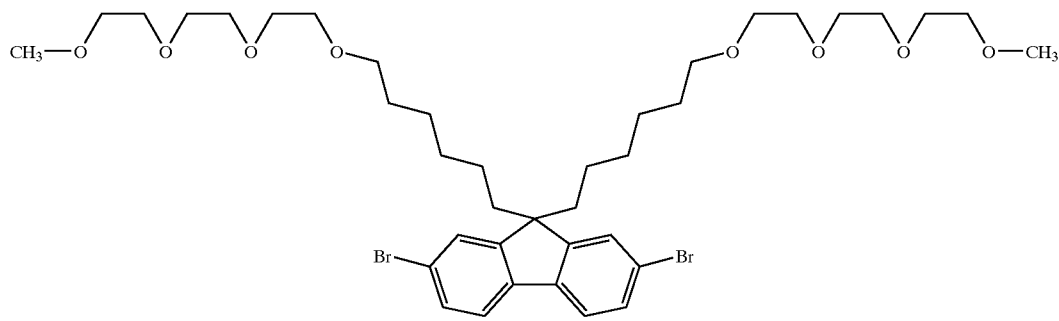

5 mmol (1.62 g) of 2,7-dibromofluorene are dissolved in 30 ml of anhydrous N,N-dimethylformamide. 10 mmol of sodium hydride (NaH), 240 mg, are then added gradually to this solution. After the mixture has been stirred at ambient temperature for six hours, 10 mmol (2.27 g) of 1-bromo-7,10,13,16-tetraoxaheptadecyl are added dropwise. The reaction mixture is then stirred at ambient temperature for a period of 12 hours. The reaction mixture is subsequently neutralized with 10 ml of water. The monomer is extracted with ether. This organic phase is then washed with an aqueous solution. The organic phase is subsequently dried over $MgSO_4$ and then evaporated under reduced pressure. This gives a yellow-colored oil. It is purified by chromatography on a silica column using pentane or hexane as eluent.

3/Synthesis of poly[9,9-bis(7,10,13,16-tetraoxaheptadecyl)fluorene-2,7-diyl]

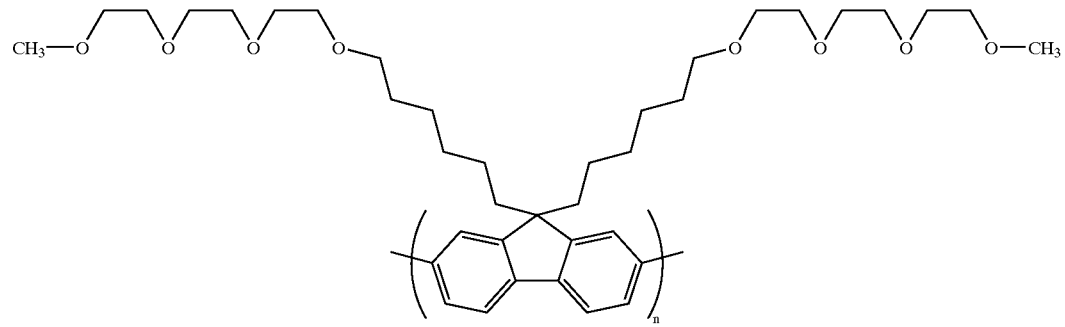

2.5 mmol (2.04 g) of 2,7-dibromo-9,9-bis(7,10,13,16-tetraoxaheptadecyl)fluorene, 0.25 mmol (65.5 mg) of triphenylphosphine, 0.125 (19.52 mg) mmol of 2,2'-bipyridyl, 0.125 mmol (16.20 mg) of nickel chloride NiCl$_2$ and 7.75 mmol (506 mg) of zinc powder (99.998% –100 mesh) are introduced into a 20 ml round-bottomed flask. Then 3 ml of anhydrous N,N-dimethylacetamide are added. The mixture is first stirred at ambient temperature for 30 minutes and then brought to a temperature of 80° C. Stirring is continued for 3 days in the absence of light. After cooling, the solution obtained is taken up in 5 ml of a methanol/concentrated HCl mixture and then evaporated to dryness. The polymer is then redissolved in the hexane. After evaporation, a yellow oil is recovered: the polymer is molten at ambient temperature.

4/Synthesis of the copolymer (initial monomer proportion 1:4) poly[9,9-bis(7,10,13,16-tetraoxa-heptadecyl)fluorene-co-9,9-(dihexyl)fluorene)]

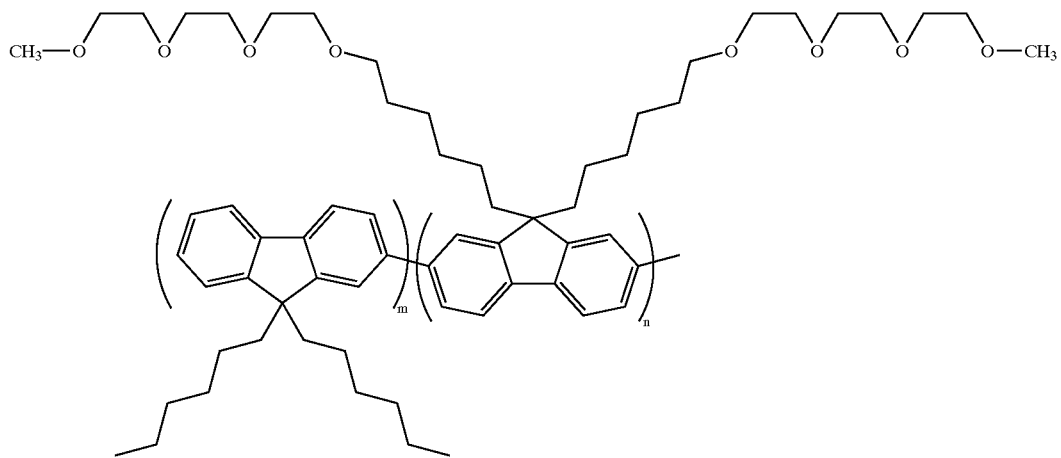

0.5 ml (312 mg) of 2,7-dibromo-9,9-bis(7,10,13,16-tetraoxaheptadecyl)fluorene, 2.0 mmol (661 mg) of 2,7-dibromo-9,9-(dihexyl)fluorene, 0.25 mmol of triphenylphosphine, 0.125 mmol of 2,2'-bipyridyl, 0.125 mmol of nickel chloride NiCl$_2$ and 7.75 mmol of zinc powder (99.998% -100 mesh) are introduced into a 20 ml round-bottomed flask. Then 3 ml of anhydrous N,N-dimethylacetamide are added. The mixture is first stirred at ambient temperature for 30 minutes and then brought to a temperature of 80° C. Stirring is continued for 3 days in the absence of light. After cooling, the solution obtained is poured into 100 ml of a methanol/concentrated HCl mixture (80/20). The polymer which then precipitates is recovered by filtration and then dried under primary vacuum. More extensive purification may be carried out by repeating this operation a number of times. Under these conditions the solid is redissolved in 5 ml of N,N-dimethylacetamide. The resulting copolymer is in the form of a light yellow solid.

EXAMPLE 2

Synthesis of the monomer 2,7-dibromo-9,9-bis(5,8,11-trioxadodecyl)fluorene

1/Synthesis of 1-bromo-5,8,11-trioxadodecane:

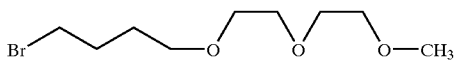

This compound is prepared in a way similar to that in paragraph 1/ of example 1) by reacting the sodium salt of diethylene glycol monomethyl ether with an excess of 1,4-dibromobutane. Column purification gives a yellow-colored oil.

2/Synthesis of the monomer 2,7-dibromo-9,9-bis(5,8,11-trioxadodecyl)fluorene:

Under the conditions of paragraph 2/ of example 1,2 equivalents of 1-bromo-5,8,11-trioxadodecane are reacted with one equivalent of 2,7-dibromofluroene in the presence of two equivalents of sodium hydride. The monomer thus obtained can be homopolymerized or copolymerized under the conditions of paragraphs 3 and 4 of example 1.

EXAMPLE 3

Preparation of the monomer of a poly-paraphenylene-vinylene possessing a flexible solvating arm

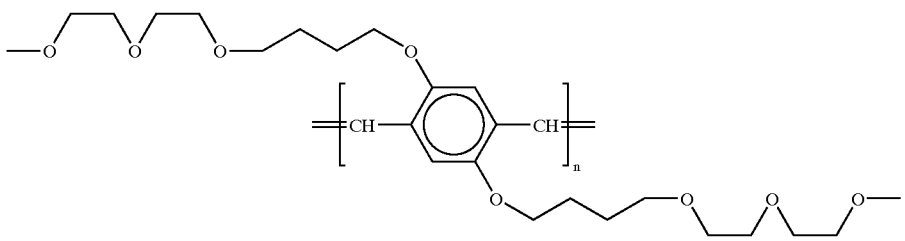

10 mmol of 2,5-dimethylhydroquinone in 25 mL of chlorobenzene, 20 mmol of 1-bromo-5,8,11-trioxadodecane, 20 mmol of sodium hydroxide in the form of a 50% aqueous solution are reacted in the presence of a phase transfer catalyst, tetrabutylammonium bromide. The 1,4-dimethyl-2, 5-bis(5,8,11-trioxadodecyloxy)benzene thus obtained is purified by chromatography. 1,4-bis(Bromomethyl-2,5-bis (5,8,11-trioxadodecyloxy)benzene is obtained by treatment with two equivalents of N-bromosuccinimide. Duplicative elimination by potassium tert-butoxide in THF gives the polymer.

EXAMPLE 4

Preparation of an Electroluminescent Diode (Copolymer+ Salt)

A stock solution is first prepared by dissolving 50 mg of lithium triflate ($LiCF_3SO_3$) in 5 ml of anhydrous cyclohexanone. Then 10 mg of poly[(9,9-bis(7,10,13,16-tetraoxaheptadecyl)fluorene-co-9,9-(dihexyl)fluorene)] are dissolved in 1 ml of this stock solution. The active layer is deposited on a glass plate (thickness 1 mm) covered with a layer of tin-doped indium oxide (thickness 200 nm) engraved beforehand in order to delimit conductive zones (cf. FIG. 1). After filtration of the solution containing the copolymer and the salt (0.2 μm filters), the active layer (copolymer+salt) is deposited on the glass/ITO substrate by spin coating. The volume of solution used is 100 μl and the rotary speed of the plate is 600 revolutions per minute.

Under these conditions, a deposit with a thickness close to 80 nm is obtained. The last step consists in depositing a metal layer on the surface of the active layer.

Before any metal deposition, the specimens are dried under primary vacuum. The specimen is then covered with a mask of which the perforated portions, which are the only ones which will allow the aluminum to pass through, have the form of the metallic electrode. An aluminum layer with a thickness close to 120 nm is thus deposited by evaporation under vacuum.

When the device is polarized under a voltage of 4.5 V directly (ITO pole positive) or inversely (aluminum pole positive), a blue luminous emission characteristic of polymers of the polyfluorine type is observed.

EXAMPLE 5

Preparation of an Electroluminescent Diode (Copolymer+ Salt+Poly(Ethylene Oxide))

An electroluminescent device may be prepared in a way which is similar to that in example 4) by starting from a stock solution containing 10 mg of lithium triflate and 10 mg of poly(ethylene oxide). In this case the luminous emission maybe observed for operating voltages of 3.5 volts.

What is claimed is:

1. A monomer of general formula A—(Q—S)$_p$ where:

A=aromatic or heteroaromatic nucleus, $1 \leq p \leq 6$

Q=carbon-based or silicon-based divalent radical, corresponding respectively to the general formulae:

$(CR^1R^2)_n$ where $R^1$ and $R^2$ H, alkyl or alkenyl containing between 1 and 4 carbon atoms and n is between 4 and 24, and $[(O—Si(R_1R_2)]_n$ where $R_1$ and $R_2$=H, alkyl or alkenyl containing between 1 and 4 carbon atoms and n is between 3 and 24

S=solvating segment consisting of an aliphatic chain containing at least one polar heteroatom, S being selected from the group consisting of:

a polyether of general formula:
—[OCH$_2$CH(R)]$_r$OR' or —[OCH(R)CH$_2$]$_r$OR'
where r is between 1 and 50
R=H or alkyl containing from 1 to 6 carbon atoms
R'=alkyl, alkenyl, aryl, arylalkyl or alkenylaryl containing from 1 to 30 carbon atoms a polyamine corresponding to the general formula:
—[N(R")CH$_2$CH(R)]$_r$N(R")R'
or —[OCH(R)CH$_2$]$_r$N(R")R' in which:
r is between 1 and 50
R and R"=H or alkyl containing 1 to 6 carbon atoms
R'=alkyl, alkenyl, aryl, arylalkyl or alkenylaryl containing from 1 to 30 carbon atoms.

2. The monomer as claimed in claim 1, characterized in that A is selected from the group consisting of the nuclei phenyl, naphthalene, pyrrole, thiophene, benzothiophene, pyridine, quinoline, carbazole, anthracene, and fluorene.

3. The monomer as claimed in claim 1, characterized in that A is selected from the group consisting of vinylene-phenyl, vinylene-naphthalene, vinylene-pyrrole, vinylene-thiophene, vinylene-benzothiophene, vinylene-pyridine, vinylene-quinoline, carbazole, vinylene-fluorene, and vinylene-anthracene.

4. The monomer as claimed in claim 1, characterized in that it has functions allowing its subsequent polymerization, wherein said functions are selected from the group consisting of halogen, amine and aldehyde functions.

5. The monomer as claimed in claim 1, corresponding to the name 2,7-dibromo-9,9-bis(7,10,13,16-tetraoxaheptadecyl)fluorene.

6. The monomer as claimed in claim 1, corresponding to the name 2,7-dibromo-9,9-bis(5,8,11-trioxadodecyl) fluorene.

7. A polymer of homopolymer or copolymer type incorporating the monomer of claim 1.

* * * * *